United States Patent [19]

Maino et al.

[11] Patent Number: 5,085,985

[45] Date of Patent: Feb. 4, 1992

[54] MONOCLONAL ANTIBODIES AND THEIR USE IN A METHOD FOR MONITORING SUBSETS OF ACTIVATED T CELLS

[75] Inventors: Vernon C. Maino; Marina E. Janszen, both of Los Altos, Calif.

[73] Assignee: Becton Dickinson & Co., Franklin Lakes, N.J.

[21] Appl. No.: 119,745

[22] Filed: Nov. 12, 1987

[51] Int. Cl.$^5$ .......................................... G01N 33/577
[52] U.S. Cl. ........................................ 435/7.24; 435/34; 435/948; 435/960; 435/973; 435/110; 436/525; 436/548
[58] Field of Search ................... 435/7, 172.2, 240.27, 435/948, 34, 7.24, 960, 973; 436/525, 548; 935/110

[56] References Cited

U.S. PATENT DOCUMENTS

| | | | |
|---|---|---|---|
| 4,364,932 | 12/1982 | Kung et al. | 424/85 |
| 4,364,934 | 12/1982 | Kung et al. | 530/808 |
| 4,515,893 | 5/1985 | Kung et al. | 435/240.27 |
| 4,515,894 | 5/1985 | Kung et al. | 435/240.27 |
| 4,515,895 | 5/1985 | Kung et al. | 435/240.27 |
| 4,550,086 | 10/1985 | Reinherz et al. | 436/506 |
| 4,599,304 | 7/1986 | Lanier et al. | 435/7 |
| 4,626,507 | 12/1986 | Trowbridge et al. | 435/240.27 |

FOREIGN PATENT DOCUMENTS 2095258 9/1982 United Kingdom.

OTHER PUBLICATIONS

Loken et al., *Journ. Immunol. Meth.*, 50, R85-R112, 1982.
Kohler et al., *Europ. Journ. Immunol.*, 6, 511-519, 1976.
Chan et al., *Biol. Abstr., 81, 82423, 1986.*
Corte e al., *Europ. Journ. Immunol., 11, 162-164, 1981.*
Bernier et al., *Journ. Immunol.*, 95, 246-253, 1965.
Manio et al., *Journ. Immunol.*, 137, 3093-3099, 1986.
Hood et al., *Immunology*, 2nd Edition, Benjamin/Cummings Publishing Company, Inc., Menlo Park, CA, 1984. pp. 66-68.
Lydyard et al., *Biochem. Soc. Trans.*, 13, 429-432, 1985.
Leukocyte Typing III, McMichael ed., Oxford Univ. Press (1987) pp. 516-526; 542-546.

*Primary Examiner*—David A. Saunders
*Attorney, Agent, or Firm*—Robert M. Hallenbeck

[57] ABSTRACT

Monoclonal antibodies which recognize activated T lymphocytes are secreted by hybridomas produced by conventional fusion and selection methodology following immunization of mice with a human lymphocyte fraction containing T lymphocytes activated by a mitrogen or an antigen. The monoclonal antibodies are used in a method to monitor subsets of activated T lymphocytes present, for example, from a patient's blood.

13 Claims, 1 Drawing Sheet

MONOCLONAL ANTIBODIES AND THEIR USE IN A METHOD FOR MONITORING SUBSETS OF ACTIVATED T CELLS

1. FIELD OF THE INVENTION

This invention relates to monoclonal antibodies which recognize activated T cells, and the use of the monoclonal antibodies in a method to monitor subsets thereof.

2. BACKGROUND OF THE INVENTION

There are two principle classes of lymphocytes involved in the immune system of humans and animals. B cells develop from haemopoietic stem cells in the bone marrow and remain in the bone marrow to undergo differentiation. Mature B cells emerge from the bone marrow and circulate freely in the body humors. B cells secrete antibodies and are responsible for humoral immune responses.

T cells likewise develop from haemopoietic stem cells in the bone marrow, but are differentiated in the thymus. Mature T cells emerge from the thymus and circulate between the tissues, lymphatics and bloodstream where they form a large percentage of the pool of recirculating small lymphocytes. They exhibit immunological specificity and are directly involved as effector cells in cell-mediated immune responses, such as graft rejection. T cells do not secrete antibodies.

It is now recognized that circulating T cells are divided into several subtypes, termed "helper," "suppressor" and "killer" T cells which have the functions of promoting a reaction, suppressing a reaction or killing (lysing) foreign cells, respectively. It is further recognized that, within these subtypes, various subsets or subpopulations exist. Circulating T cells are generally nonproliferative and are commonly referred to as non-activated, unstimulated, resting or normal cells. In this disclosure, such nonproliferating T cells are hereinafter referred to as resting T cells. Under some circumstances, for example, when in the presence of a specific antigen such as Leu 4, or a mitogen, T cells do proliferate. Proliferating T cells are generally referred to as activated cells. Activation of T cells results in expression of surface antigens not expressed by normal cells.

The ability to identify and enumerate classes, types and subsets of T-lymphocytes is important for diagnosis or treatment of various immunoregulatory disorders. For example, rheumatoid arthritis and malignancies are associated with an imbalance of T cell subsets.

The identification and suppression of human T cell classes and subclasses have been accomplished by using isolated autoantibodies or polyclonal antisera for human T cells. Such preparations have all the disadvantages, such as heterogeneity and unwanted side reactions, associated with polyclonal antibodies.

Monoclonal antibodies to resting T cells have been described. U.S. Pat. Nos. 4,515,893 and 4,515,894 to Kung et al. disclose monoclonal antibodies which react with essentially all resting human peripheral T cells. U.S. Pat. No. 4,515,895 to Kung et al. discloses monoclonal antibodies which react with essentially all resting human peripheral helper T cells. U.S. Pat. No. 4,364,932 to Kung et al. discloses monoclonal antibodies which react with the cytotoxic and suppressor T cell subset designated as $TH_2^+$. A monoclonal antibody which binds specifically to the surface recognition structure of a human T cell clone is disclosed in U.S. Pat. No. 4,550,086 to Reinherz et al. A monoclonal antibody which recognizes a surface glycoprotein on proliferating blood cells which is absent on normal peripheral blood cells is disclosed in U.S. Pat. No. 4,626,507 to Trowbridge et al.

There is a need for a method to demonstrate or detect activated T lymphocytes and/or subsets thereof, whereby conditions such as autoimmune diseases and transplantation reactions may be monitored. The present invention provides such a method and also monoclonal antibodies for fulfilling this need.

SUMMARY OF THE INVENTION

One aspect of the present invention is a monoclonal antibody reactive with activated T lymphocytes, but essentially unreactive with resting T lymphocytes. The antibody is produced preferably by fusing mouse myeloma cells with lymphocytes from a mouse immunized with a sample of peripheral blood lymphocytes (hereinafter referred to as PBL) containing activated T lymphocytes. The preferred antibody is produced when immunization is carried out with T lymphocytes activated by an antigen, such as Leu 4 or by a T cell mitogen, preferably phytohemagglutinin (hereinafter referred to as PHA). The preferred antibody which is produced is unreactive to T cell line HUT 78 and B cell line SB and recognizes activated Leu 1 (CD5), Leu 2 (CD8), Leu 3 (CD4) and Leu 4 (CD3) cell subsets. The most preferred monoclonal antibodies are designated as anti L-35 and anti L-36 and are secreted by hybridomas identified as ATCC HB 9050 and ATCC HB 9051 respectively. Anti L-35 and anti L-36 react specifically with heretofore undisclosed antigens, identified as L-35 and L-36 respectively, expressed by activated T lymphocytes.

Another aspect of the present invention is a method for monitoring subpopulations of leukocytes in a cell sample by detecting antigens expressed when the leukocytes undergo activation. A plurality of monoclonal antibodies, including at least one monoclonal antibody prepared in accordance with the invention herein disclosed, is conjugated to detectable labels, and the antibodies are combined in a suitable fluid with a cell sample containing activated leukocytes. The label-conjugated antibodies bind to antigens expressed by the activated leukocytes. After binding, the labels are caused to provide signals which are detected. Subpopulations of the activated leukocytes in the cell sample are distinguished and may be monitored by characteristics of the signals.

In a preferred embodiment of the method of the invention, subpopulations of activated T lymphocytes in a human blood sample are monitored by detection of antigens expressed by the T lymphocytes. If the antigens are on the surface of the cells, the labels are preferably fluorescent markers and the signal to be detected is fluorescence emission. If the antigens are secreted into the serum, the labels are preferably enzymes and signals conventional in enzyme immunoassay, such as a substrate color change, are detected.

In the most preferred embodiment of the present method, antigens expressed on the surface of T lymphocytes in a blood sample are detected by well-known flow cytometry techniques using anti L-35 conjugated to fluorescein or anti L-36 conjugated to phycoerythrin B in conjunction with the known anti-Leu-4 monoclonal antibody.

Thus, the invention provides new monoclonal antibodies which recognize and react with heretofore undisclosed antigens expressed by subpopulations of activated, but not resting, leukocytes. The monoclonal antibodies are secreted by hybridomas produced by conventional fusion and selection techniques after immunization of mice with activated T lymphocytes in a lymphocyte fraction isolated from peripheral human blood. Because the antibodies do not recognize resting T cells, they have unique application in a method for the isolation and characterization of activated T cell populations and may therefore have therapeutic applications in various pathological conditions associated with T cell dysfunction. Anti L-35 and anti L-36 are IgG2a,k monoclonal antibodies and, therefore, bind Protein A, making them useful for immunoprecipitation and isolation of the cell surface protein which they recognize. Also because they are IgG2a,k antibodies, they fix complement and, therefore, may be used for removal of antigen positive cells.

DETAILED DESCRIPTION OF THE INVENTION

Figure 1:
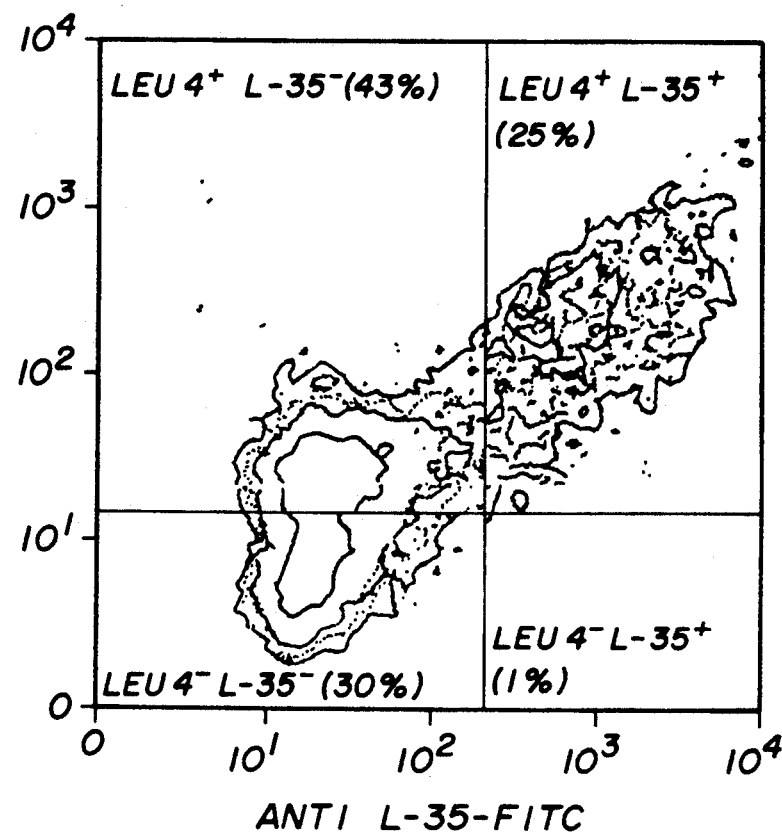
FIG. 1 shows a two dimensional contour map of multiple subpopulations of activated T lymphocytes produced by a two-color flow cytometry analysis performed in accordance with the method of the invention.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

Definitions

As used herein:

Monitoring—refers to any one or more of analyzing, characterizing, distinguishing, identifying, sorting, separating or counting of cells, cell groups or bilogical particles on the basis of cell or particle properties or signals representative thereof.

Lymphocyte fraction—refers to an isolated suspension of cells from a sample of body tissue, such as spleen, or body fluid, such as peripheral blood, either whole or prepared, which includes substantially all of the leukocytes, including NK cells, monocytes, macrophages, granulocytes, B lymphocytes and T lymphocytes, present in the sample of body fluid or tissue.

Monoclonal antibody—A homogeneous antibody obtained from a hybrid cell line (a hybridoma) which is usually produced by the fusion of mouse myeloma cells to spleen cells, first described by Kohler and Milstein (*Nature* 256, 495–497, 1975). The specificity of a particular monoclonal antibody is influenced principally by the type of antigen employed to immunize the host and the selection technique used to isolate the host cell which is subsequently fused to the myeloma cell to produce the hybrid cell. It is now recognized that a substantially functional equivalent for a particular monoclonal antibody can be created by repetition of the immunization process with the same or related antigens.

FACS ™ Cell Sorter—A fluorescence activated cell sorter, manufactured by Becton Dickinson Immunocytometry Systems, San Jose, Calif., which is useful for Monitoring. FACS apparatus commonly includes a light source, usually a laser, and several detectors for the detection of subpopulations of cells in a mixture using light scatter or light emission parameters. In these devices, fluorescence detectors may be used in conjunction with the fluorescently stained cells to be detected in the mixture of cells in the sample being analyzed. In some cases, a separate light source is used to excite each different type of dye or stain which has been bound onto a cell to be studied. Another, but different, instrument, useful for Monitoring and known as the FACS ™ Analyzer, manufactured by BDIS employs a mercury arc lamp source for light excitation, instead of a laser, and normally does not have cell sorting capabilities.

Anti-Leu-4—A designation for a commercially available monoclonal antibody which recognizes both resting and activated T lymphocytes expressing the CD3 antigen.

In accordance with one aspect of the present invention, Monoclonal antibodies recognizing activated T lymphocytes are produced. A Lymphocyte Fraction containing T lymphocytes to be activated and used for immunization is isolated from a body fluid such as, for example, peripheral blood, or from a tissue section. Preferably, a T Lymphocyte Fraction containing substantially all of the mononuclear cells is isolated from human peripheral blood. Isolation of the cell sample may be carried out by any suitable method, such as the Ficoll-Hypaque density gradient technique as described by T. Abo et al., J. of Immunol. 127, 1024 (1981). It is understood, however, that isolation of the cell sample to be used for immunization need not utilize Ficoll-Hypaque or similar separation. A total lymphocyte fraction, for example, may be provided on the basis of other biophysical properties of such cells, such as volume and light scatter, and then collecting or detecting such cells in an unseparated blood sample using appropriate instrumentation such as a FACS ™ Cell Sorter or FACS ™ Analyzer.

The isolated cell fraction containing resting T lymphocytes is suspended in a suitable tissue culture fluid, such as, for example, RPMI (Roswell Park Memorial Institute) 1640 medium or phosphate buffered saline (PBS), and treated with an activator to activate at least a portion of the T lymphocytes. Suitable activators may be, for example, an antigen or a T cell mitogen. Any antigen such as, for example Leu 4, which recognizes a receptor on the surface of the T lymphocyte may be used for activation. Useful mitogens are plant lectins such as Concanavilin A, wheat germ agglutinin, and preferably, PHA.

Generation and selection of the monoclonal antibodies of this invention are carried out by standard methods well-known in the art. A brief description of the procedure is given below, and details are presented in the Example.

The cell fraction containing activated T lymphocytes, isolated and activated as above, is used to immunize an appropriate strain of mice, preferably BALB C mice. An immunization route and schedule, which may be varied, is used to activate antibody-producing lymphocytes in the mice.

Spleen cells are isolated from the immunized mice and fused with cells of an appropriate mouse myeloma cell line to provide hybridomas. Suitable techniques for effecting fusion are described by Kohler et al., *Eur. J. Immunol.* 6, 511 (1976) and by Gefter et. al., *Somatic Cell Genet.* 3,231, (1977). The preferred myeloma cell line is that designated as SP-2/0 AZ14. Hybridoma selection is carried out according to the procedure of Buck et. al., Production of Human Monoclonal Antibodies in: *Monoclonal Antibodies and Functional Cell Lines.* (R. H. Kennett, K. B. Bechtol, and T. J. McKearn, eds.) Plenum Publishing Corp., New York. 1984 p. 275 using hypoxanthine-azaserine selection medium. Hybridomas grow in this medium and may be separated from unfused myeloma cells and spleen cells, which die shortly after fusion.

Hybridomas which secrete monoclonal antibodies are cultured to give clones from individual hybridoma cells to establish continuity of proliferation with stable genetic composition over several generations. Hybridoma clones secreting antibodies reactive with activated T lymphocytes in accordance with the present invention may be identified by selecting those clones secreting antibodies which are reactive with PBL activated with PHA or Leu-4, but which are essentially unreactive with resting PBL. Other criteria used in the selection include unreactivity to T cell line HUT 78 or B cell line SB as determined by a conventional ELISA-based cell binding assay or flow cytometric TM analysis.

Two monoclonal antibodies, hereinafter referred to as anti L-35 and anti L-36, are isolated by this selection protocol and may be obtained in quantity by injection into BALB/C mice, isolation from ascites fluid and purification by conventional protein A-sepharose affinity chromatography. Anti L-35 immunoprecipitates an antigenic bimolecular complex, hereinafter referred to as L-35, expressed by cellular components of PBL, including activated T lymphocytes, consisting of proteins having molecular weights of about 32,000 and 96,000 daltons. The 32,000 dalton protein, however, appears only when PHA is used as a mitogen to activate T lymphocytes. Thus, the 32,000 protein may be a subunit of PHA. Anti L-36 recognizes an antigenic protein, hereinafter referred to as L-36, having a molecular weight of about 90,000 daltons.

The hybridomas secreting monoclonal antibodies anti L-35 and anti L-36 were deposited for permanent maintenance with the American Type Culture Collection, Rockville, Md. on Apr. 21, 1986, and have been designated as ATCC HB 9050 and ATCC HB 9051, respectively.

In another aspect of the invention, one or more monoclonal antibodies which recognize activated T lymphocytes may be used in a method to monitor subsets of activated T lymphocytes. Preferably, two or more antibodies, including one antibody of the present invention, such as anti L-35 and anti L-36 are used, however, it is contemplated to perform the method of the invention with any pair of monoclonal antibodies which recognize activated T lymphocytes, including known anti T-cell antibodies such as, for example, anti-Leu-4.

For two color flow cytometric TM analysis the two antibodies are conjugated to different fluorescent dyes by any conventional procedure, as, for example, the procedures described by Wofsy et. al., "Modification and Use of Antibodies to Label Cell Surface Antigens," *Selected Methods in Cellular Immunology*, B. B. Mishell and S. M. Siigi, ed., W. H. Freeman and Co. (1980). Various pairs of dyes may be used, and in general, the two dyes should have a detectable fluorescence emission difference, preferably 25 nm or greater. Useful dyes may be selected from the fluorescein, rhodamine, Texas Red, or phycobiliprotein groups as exemplified by phycoerythrin B and allophycocyanin. Exemplary of, but not limited to, useful dye pairs are fluorescein or rhodamine conjugated to one antibody and phycoerythrin B or Texas Red conjugated to the other antibody. Particularly preferred dye combinations are fluorescein-Texas Red and fluorescein-phycoerythrin B in which fluorescein is conjugated to one monoclonal antibody by reaction with fluorescein isothiocyanate, and Texas Red or phycoerythrin B is conjugated to the second monoclonal antibody by the well-known biotin-avidin coupling reaction. In this last-mentioned procedure, the dye is first conjugated to avidin and the second antibody is conjugated to biotin. When these two components are brought together, the biotin and avidin couple to provide the dye-conjugated antibody.

The dye-conjugated monoclonal antibodies may be combined in a suitable fluid with a lymphocyte fraction, isolated from a patient's peripheral blood as described above, so that the antibodies bind to activated T lymphocytes in the sample and thereby provide labeled T lymphocytes. If desired, an incubation step may be used to promote binding.

The labeled T lymphocytes may be analyzed with a flow cytometer for their light scatter or fluorescence properties, or both parameters may be analyzed simultaneously. Scatter signals may be detected in both the forward and wide angle directions, and may be used to identify subpopulations of activated cells based on cell size, morphology and granularity. Fluorescence emission may be detected with a fluorescence microscope, or preferably, with a flow cytometer. Two color cell analysis may be performed as described by Parks, et al., Flow Cytometry and Fluorescence-Activated Cell Sorting. *Handbook of Experimental Immunology*, 4th ed. D. M. Weir, L. A. Herzenberg, C. C. Blackwell, and L. A. Herzenberg eds. Blackwell Scientific Publications, Edinburg, 1984. The labeled cells may be passed, substantially one at a time, through a flow cytometer equipped with one or more lasers, such as argon and helium-neon 30 mW lasers, to provide excitation energy to excite the two dyes. The wavelength of excitation light depends on the dyes used, and, in some circumstances, a single light source may be used to excite multiple fluorescent dyes. Thus, fluorescein and phycoerythrin B may be excited by incident light from an argon laser using about 488 nm, and Texas Red may be excited by the helium-neon laser at about 568 nm.

The results of typical experiments in which a lymphocyte fraction containing activated T cells is treated in accordance with the hereinabove described method are set forth in FIGS. 1 and 2. In the experiment leading to FIG. 1, the lymphocyte fraction is reacted with monoclonal antibodies anti L-35 conjugated to fluorescein (FITC) and anti-Leu-4 conjugated to phycoerythrin B (PE), and analyzed by flow cytometry. It is seen that four subpopulations of activated T cells, designated as Leu 4+, L-35− (43%); Leu 4+, L-35+ (25); Leu 4−, L-35+ (1%); and Leu 4−, L-35− (30%) have been distinguished based on recognition (+) or nonrecognition (−) of the two monoclonal antibodies in accordance with their relative positions with respect to the Leu 4 "Y" axis and the L-35 "X" axis. The abundance of each subpopulation in the total population of labeled T lymphocytes is given by the percentages in parentheses. Thus, for example, FIG. 1 indicates a 25% subpopulation expressing L-35 and Leu-4 antigens in the total population of activated T cells.

Figure 2:
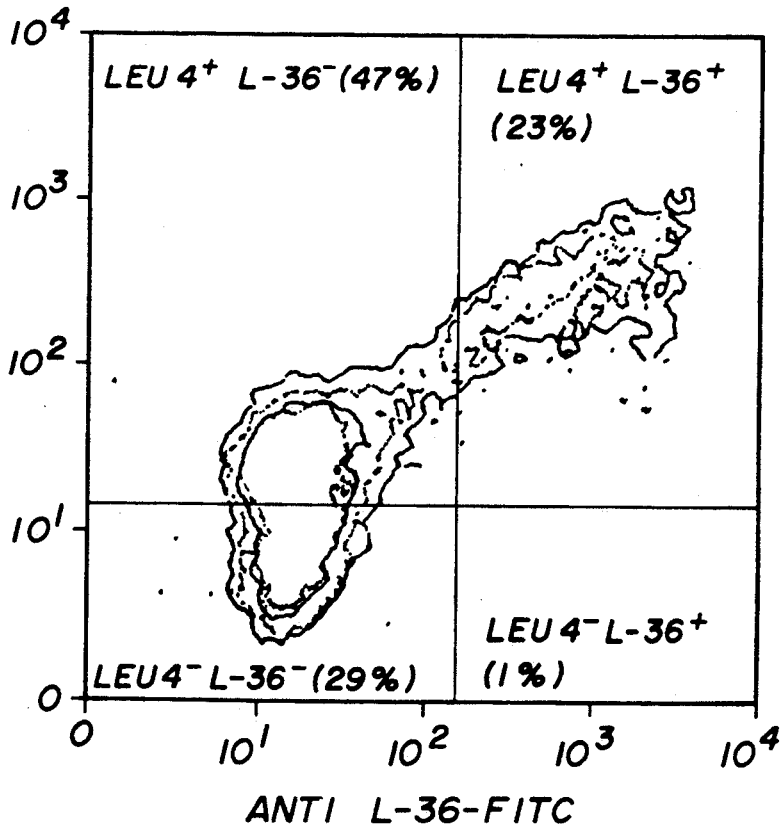
FIG. 2 shows a similar contour map of multiple subpopulations produced using a different pair of monoclonal antibody dye conjugates.

FIG. 2 shows a similar display of two color cell analysis consequent to reaction of the lymphocyte fraction containing activated T cells with monoclonal antibodies anti-Leu-4-phycoerythrin B and anti L-36-fluorescein. Again, four subpopulations, as in FIG. 1 are shown having relative percentages of 47%, 23%, 1% and 29% for each of the quadrants.

The method of the invention may also be used to monitor subsets of activated T lymphocytes in a blood sample which express and release antigens into the serum. In this embodiment of the invention, a conventional immunoassay may be performed in which the monoclonal antibodies are conjugated to a fluorescent dye as described above, or to an enzyme, such as a peroxide, and combined with a serum sample in a suitable fluid so that the antibodies bind to serum T cell antigens. Antigens bound to the dye- or enzyme-conjugated antibodies may be separated from unbound antigens and antibodies by any conventional procedure. Preferably, the antibodies are attached to a solid support and unbound antigens and antibodies in the fluid phase are removed by decantation and washing. The bound T cell antigens are detected, and, if desired, their concentrations determined by signals, such as fluorescence emission or substrate color change, standard to conventional fluorescence or enzyme immunoassay. Subpopulations of the activated T lymphocytes may be monitored as a function of the detected signals.

Subsets of activated T lymphocytes in a body tissue may also be monitored in accordance with the method of the invention. Thin tissue slices having antigens on the surfaces of the activated T cells are suspended in a fluid and the antigens detected after binding to dye- or enzyme-conjugated monoclonal antibodies as previously described. Preferably, bound and unbound antigens are separated by washing the tissue slices after binding.

In another embodiment of the invention, the monoclonal antibody of the invention may be conjugated to gold by conventional methodology. The conjugate is contacted in a fluid with a cell sample containing activated T lymphocytes so that an antigen expressed on the surface of the T cell may bind specifically to the gold-conjugated antibody to give an immunoprecipitate which may be detected by conventional light or electron microscopy.

The subpopulations of activated T lymphocytes may, if desired, be physically separated by appropriate manipulations of the flow cytometer having sorting capabilities, well-known to those skilled in the use of the instrument.

EXAMPLE

Abbreviations used: MAb, monoclonal antibody(ies); PHA, phytohemagglutinin; FACS, fluorescence activated cell sorter; PE, phycoerythrin.

T cell Activation

Heparinized venous blood was obtained from the Stanford University blood bank. After Ficoll-Hypaque separation, adherent cells (monocytes) were removed by adsorption to plastic Petri dishes (30 min at 37° C.). PHA (Gibco, Grand Island, N.Y.) was used at a concentration of 2% to stimulate resting, adherent, cell-depleted peripheral T cells in RPMI medium (Gibco) with 2.5% fetal calf serum (KC Biological, Larexa, Kan.). Cells were cultured in a humidified incubator at 37° C. at a concentration of $2 \times 10^6$ cells/ml in 25 cm$^2$ flasks. Activation of PBLs with anti-Leu-4 was performed in a similar fashion employing 0.1 g/ml of purified anti-Leu-4 (BDIS) antibody. At various times, activated and control cultures were harvested, washed three times with PBS containing 1% bovine serum albumin (BSA) and 5% N-acetylgalactosamine (Sigma, St. Louis, Mo.). Alloantigen-stimulated peripheral T cells were obtained by co-culturing with a 1:1 ratio of irradiated SB cell line or allogeneic PBL.

To assay for proliferation, $2 \times 10^5$ cells stimulated with PHA or anti-Leu-4 as described above were cultured in 96-well plates (Microtest III, Becton Dickinson, Oxnard, Calif.) in a total volume of 0.2 ml RPMI 1640 supplemented as above. Control cultures contained cells alone. At intervals after initiation of cultures, each well was pulsed with 1 Ci of tritiated thymidine ($^3$H-TdR, Amersham,) for 18 hrs. Cells were harvested using a Cambridge cell harvester, and samples were counted in a Beckman liquid scintillation counter.

Production of Anti L-35 and Anti L-36 Antibodies

Six week old female BALB/c mice obtained from the Institute for Medical Research, San Jose, Calif., were immunized intravenously (i.v.) with normal PBL which had been incubated for three days in the presence of 2% phytohemagglutinin (PHA). Two weeks later, a second intraperitoneal (i.p.) injection was given of $1 \times 10^7$ 5 day PHA-activated PBL and 1 week later a third injection of $1 \times 10^7$ 2 day activated PBL was performed. Three days after the final immunization, the spleen was removed and $5 \times 10^7$ spleen cells were fused with $1 \times 10^7$ SP-2/0 AZ14 myeloma cells and resulting hybridomas were screened using the hypoxanthine-azaserine selection medium (Buck et. al., supra.). Hybridoma supernatants were initially screened for selective reactivity with PHA-activated T cells by using a cell ELISA assay. A quantity of $4 \times 10^5$ activated T cells or transformed cell lines was added to each well of polyvinylchloride microtiter plates (Becton Dickinson, Oxnard, Calif.). Hybridoma antibody binding was detected using a polyvalent anti-mouse Ig reagent conjugated to horseradish peroxidase (Tago, Burlingame, Calif.). Supernatants which demonstrated positive reactivity with PHA-activated PBL but which did not react with resting PBL or HUT-78 (T cell leukemia) or SB (B lymphoblatoid) transformed cell lines were selected for further cloning and analysis. Selected clones were further screened by using indirect immunofluorescence and flow cytometric analysis. Two clones were selected which demonstrated reactivity with activated but not resting T cells and furthermore did not bind to either HUT-78 or SB cells.

Purification and Conjugation of Antibodies

Selected hybridoma clones were serially passaged by i.p. injection into BALB/cj mice primed with pristane. Ascites were collected, ultracentrifuged, and stored at −70° C. until use. L-35 and L-36 antibodies were determined by ELISA to be IgG2$_a$. Immunoglobulin was purified from ascites fluid by ammonium sulfate precipitation and protein-A sepharose affinity chromatography. Fluorescein was conjugated to the antibodies by the method of Wofsy et. al. (supra).

Molecular Specificity

T cells were activated with PHA for 48 hours. After activation, the T cells were variously labeled with $^{125}I$ (Amersham) by using chloroglycouril (Iodogen) or lactoperoxidase (Sigma) and with [$^{35}S$] methionine (100 Ci/mole, Amersham). Lysates were obtained after labeling and supernatants were treated twice with 1% ovalbumin and *Staphylococcus aureus* Cowan I strain (SaCI). Samples of immunoprecipitates derived therefrom were applied to 10% sodium dodecyl sulfate-polyacrylimide gels (SDS-PAGE, Bio-Rad). Reference markers including $\beta$-galactosidase, phosphorylase B, albumin, ovalbumin, carbonic anhydrase and lysozyme were used.

The 96,000 protein was identified by anti-L-35 in both $^{125}I$- and $^{35}S$-labeled lysates. In contrast, the 32,000 protein was identified in $^{125}I$-labeled lysates only. The 32,000 protein also did not appear unless the T cells had been activated for more than 12 hours. Similarly, the 32,000 protein was not identified by anti-L-35 in Con A or anti-Leu-4 activated cells. It appears, therefore, that anti-L-35 recognizes a 96,000 protein cell surface antigen or activated T cells that co-precipitates with a subunit of PHA when this lectin is used as a mitogen.

Flow Cytometry

Immunofluorescence and FACS analysis were performed as described by Loken et al., J. Immunol. Methods 50, R85 (1982). Isotype matched fluorochrome-conjugated myeloma proteins or nonreactive monoclonal antibodies were used to control for Fc binding. All procedures were performed in PBS containing 0.1% NaN$_3$ at 4° C. For each sample 10,000 cells were analyzed; the percentage of cells positively stained was calculated after subtracting the percentage of cells stained with isotype matched control antibodies. Prior to flow cytometric analysis, PHA-activated cells were washed three times in 3% N-acetylgalactosamine and purified on ficoll-hypaque (Pharmacia) to remove dead cells. Flow cytometry was performed with a FACS TM 440 instrument (Becton Dickinson, San Jose, Calif.). Data were processed on a Hewlett Packard (Palo Alto, Calif.) 9816 microcomputer using Consort TM 30 software (Becton Dickinson, San Jose, Calif.).

Thus, monoclonal antibodies which recognize activated leukocytes, preferably activated T lymphocytes in a blood sample are prepared by a technique using a leukocyte fraction containing activated T lymphocytes as the immunogen. The monoclonal antibodies recognize antigens which are expressed by activated T lymphocytes either on the cell surface or into the serum, but which are essentially not expressed by resting T lymphocytes. The antibodies are used in a method to monitor subpopulations of activated T lymphocytes making them valuable for monitoring pathological conditions associated with dysfunction of activated T cells.

What is claimed is:

1. A method for monitoring subpopulations of activated T lymphocytes in a sample comprising the steps of:
    (a) isolating a cell sample containing activated T lymphocytes;
    (b) combining said cell sample with a first monoclonal antibody selected from the group consisting of anti L-35 (ATCC HB 9050) and anti L-36 (ATCC HB 9051), said first monoclonal antibody being conjugated to a first fluorescent dye, and with a second monoclonal antibody selected from the group consisting of anti-CD5, anti-CD8, anti-CD4 and anti-CD3 monoclonal antibodies, said second monoclonal antibody being conjugated to a second fluorescent dye, said first and second fluorescent dyes having emission wavelengths which differ a sufficient amount to produce separately detectable signals, wherein said first and second monoclonal antibodies bind to said activated T lymphocytes;
    (c) detecting fluorescence emission from said first and second fluorescent dyes; and
    (d) monitoring subpopulations of activated T lymphocytes in said sample as a function of said detected fluorescence emission.

2. The method in accordance with claim 1 wherein said cell sample is isolated from said sample by density gradient separation.

3. The method in accordance with claim 1 wherein said first and second fluorescent dyes are selected from the group of dyes consisting of fluorescein, rhodamine, Texas Red, phycoerythrin B and allophycocyanin.

4. The method in accordance with claim 3 wherein said first fluorescent dye is fluorescein.

5. The method in accordance with claim 3 wherein said second fluorescent dye is phycoerythrin B.

6. The method of claim 1 wherein the sample is isolated from peripheral blood.

7. A method for monitoring subpopulations of activated leukocytes in a cell sample comprising the steps of:
    (a) combining a cell sample containing activated leukocytes with a monoclonal antibody conjugated to a detectable label, said antibody being selected from the group consisting of anti L-35 (ATCC HB 9050) and anti L-36 (ATTCC HB 9051), where said monoclonal antibody binds to said activated leukocytes;
    (b) causing said label to provide a detectable signal;
    (c) detecting said signal; and
    (d) monitoring subpopulations of activated leukocytes in said cell sample by characteristics of said signal.

8. The method in accordance with claim 7 wherein said cell sample is isolated from a human peripheral blood sample.

9. The method in accordance with claim 7 wherein said label is a fluorescent dye and said signal is fluorescence emission.

10. The method in accordance with claim 7 wherein said label is an enzyme and said signal is associated with a change in color of a substrate upon which said enzyme acts.

11. The method in accordance with claim 7 wherein said label is gold.

12. A method for monitoring subpopulations of activated human T lymphocytes in a sample comprising the steps of:
    (a) isolating a cell sample containing activated T lymphocytes from a human blood sample;
    (b) combining said cell sample with a monoclonal antibody selected from the group consisting of anti L-35 (ATTCC HA 9050) and anti L-36 (ATCC HB 9051), said antibody being conjugated to fluorescein, and with an anti-CD3 monoclonal antibody, said anti-CD3 being conjugated to phycoerythrin B, whereby said antibodies bind to said activated T lymphocytes to give labeled T lymphocytes;

(c) detecting two-color fluorescence emission from said labeled T lymphocytes; and (d) monitoring subpopulations of activated T lymphocytes in said blood sample as a function of said detected two-color fluorescence emission.

13. A method for monitoring subpopulations of activated T lymphocytes in a body tissue comprising the steps of:

(a) isolating a sample of a body tissue containing activated T lymphoctyes having antigens expressed on the surfaces thereof;

(b) adding to said tissue a first monoclonal antibody selected from the group consisting of anti L-35 (ATCC HB 9050) and anti L-36 (ATCC HB 9051), said first antibody being conjugated to a first fluorescent dye, and a second monoclonal antibody selected from the group consisting of anti-CD5, anti-CD8, anti-CD4 and anti-CD3 monoclonal antibodies, said second antibody being conjugated to a second fluorescent dye, said first and second dyes having emission wavelengths which differ by at least 25 nm, wherein said antigens on said activated T lymphocytes bind to said first and second antibodies to give labeled T lymphocytes;

(c) subjecting said labeled T lymphocytes to excitation light to cause fluorescence from said labeled T lymphocytes;

(d) detecting fluorescence emission from said labeled T lymphocytes; and (e) monitoring subpopulations of activated T lymphocytes in said tissue as a function of said detected fluorescence emission.

* * * * *